United States Patent [19]

Homiger et al.

[11] Patent Number: 5,273,750
[45] Date of Patent: Dec. 28, 1993

[54] UNCROSSLINKED HYDROGEL, PROCESS FOR ITS PREPARATION AND ITS USES AS AN ARTICLE FOR MEDICAL AND/OR SURGICAL PURPOSES SUCH AS TUBES, FILMS, JOINTS, IMPLANTS AND THE LIKE, PARTICULARLY IN OPHTHALMOLOGY

[75] Inventors: Jiri Homiger, Villejuif; Laurent Laroche, Paris, both of France

[73] Assignee: Institute National de la Sante et de la Recherche Medicale- Inserm, Paris, France

[21] Appl. No.: 617,917

[22] Filed: Nov. 21, 1990

Related U.S. Application Data

[63] Continuation of Ser. No. 345,944, May 1, 1989, abandoned.

[30] Foreign Application Priority Data

May 2, 1988 [FR] France .................. 88 05856

[51] Int. Cl.$^5$ .................. A61L 27/00; B29D 11/00
[52] U.S. Cl. .................. 424/427; 424/428; 424/429; 604/294; 623/4; 623/5; 623/6; 528/495
[58] Field of Search .................. 424/427, 428, 429; 528/495

[56] References Cited

U.S. PATENT DOCUMENTS

| | | | |
|---|---|---|---|
| 3,260,707 | 7/1966 | Caldwell et al. | 526/342 |
| 3,873,143 | 10/1969 | Tanaka | 428/364 |
| 4,173,606 | 11/1979 | Stoy et al. | 528/281 |
| 4,228,056 | 10/1980 | Stoy et al. | 526/221 |
| 4,631,188 | 12/1986 | Stoy et al. | 525/294 |
| 4,640,965 | 2/1987 | Falcetta et al. | 526/246 |
| 4,731,079 | 3/1988 | Stoy et al. | 128/303 R |
| 4,808,182 | 2/1989 | Barrett | 623/6 |

FOREIGN PATENT DOCUMENTS

2028956 12/1970 Fed. Rep. of Germany .
2508416 9/1976 Fed. Rep. of Germany .

Primary Examiner—Thurman K. Page
Assistant Examiner—Peter F. Kulkosky
Attorney, Agent, or Firm—Bell, Seltzer, Park & Gibson

[57] ABSTRACT

The invention relates to an uncrosslinked hydrogel, its process of preparation as well as its uses as an article for medical and/or surgical purposes such as tubes, filaments, films, joints, implants and the like, especially in ophthalmology. The uncrosslinked hydrogel has a relatively high water content and is constituted from a liquid starting composition which comprises 2 to 50% of a copolymer of acrylonitrile and an olefinically unsaturated comonomer bearing aninic groups, possible salified, the molar ratio arcylonitrile-comonomer being comprised between 90:10 and 100:0, a suitable solvent and a suitable non-solvent of said copolymer. The ratio solvent/non-solvent is comprised between 500:1 and 0.5:1 by weight, said hydrogel having a microporous structure, an ionic capacity comprised between 0 and 500 mEq/kg of gel, a hydric content compressed between 50 and 98% and having an aptitude for permanent deformation under stress, even at a temperature below 40° C.

9 Claims, 2 Drawing Sheets

UNCROSSLINKED HYDROGEL, PROCESS FOR ITS PREPARATION AND ITS USES AS AN ARTICLE FOR MEDICAL AND/OR SURGICAL PURPOSES SUCH AS TUBES, FILMS, JOINTS, IMPLANTS AND THE LIKE, PARTICULARLY IN OPHTHALMOLOGY

This is a continuation of co-pending application Ser. No. 07/345,944, filed May 1, 1989, now abandoned.

BACKGROUND OF THE INVENTION

The present invention relates to an uncrosslinked hydrogel, to its process of preparation as well as to its applications as an article for medical and/or surgical purposes such as tubes, filaments, films, joints, implants and the like, particularly in ophthalmology.

It has already been proposed, to employ polymers in hydrogel form having a relatively high water content whilst having improved mechanical and optical properties (European patent No. 188 110 and U.S. Pat. Nos. 4,379,864 and 4,543,371), for ophthalmic purposes.

However, the product described in U.S. Pat. Nos. 4,379,864 and 4,543,371 do not show a high water content; these polymers lose, in fact, the required mechanical properties, particularly for their use as an implant, when the water content is high.

As regards the hydrogel described in European patent application No. 188 110, they do not show properties of good tolerance, particularly required for an implant, to the extent that the ionic characteristics and in particular the electronegativity of the polymer does not permit good tolerance of the latter to be envisaged.

This is why Applicant has sought in another direction for a solution to the problem set, which is that of providing hydrogels having high biocompatibility for their use in the preparation of articles for medical or surgical purposes which are highly reliable and in particular ocular implants enabling a suitable permeability to be obtained to different biological molecules, said implants, not showing, consequently, the drawbacks of known implants.

Patent FR 2 529 464 described biocompatible materials in the form of hollow fibers or membranes. These biomaterials are treated by a plurality of drawings to produce a suitable permeability and showing for this reason, a different structure, namely of membranes or hollow fibers for hemodialysis and/or hemofiltration.

Patent DE-A-2028956 described a hydrogel which comprises many ionic groups, said hydrogel not showing the suitable biocompatibility sought by Applicant.

Applicant unexpectedly has found that certain biomaterials under particular condition, have considerable advantages, especially in the field of ocular implants.

It is, in this respect, an object of the invention to provide an uncrosslinked hydrogel with improved mechanical properties and with a high water content as well as its method of preparation which responds better to the necessities of practice than the hydrogels of the prior art, particularly in that they have the advantage of conferring on said hydrogels a character of inertia with respect to biological cells.

It is also an object of the invention to provide articles constituted by or comprising said hydrogel. The use of said articles in surgery and in medicine is also an object of the invention. Among said article, may be mentioned especially ocular implants which show besides the character of inertia with respect to biological cells:

the following optical properties:
perfect transparency in visible light,
absorption of ultra-violet rays at 280 nm,
refractive index close to that of the cornea.
physico-chemical properties such as:
high permeability to water, to physiological serum, to small and medium-sized molecules, assuring the migration of nutrient substances for the cornea as well as all of the metabolites,
permeability to dissolved gases ($O_2$, $CO_2$), highly hydrophilic
a chemical nature devoid of toxic groups, of heavy metals, of remaining catalysts and of free monomers and of solvent easy to use,
dimensional stability, especially in a 0.9% chloride solution
particular biological properties such as:
be non-bioresorbable in the physiological medium,
have good resistance to aging in this medium, that is to say not showing opacification, coloration or degradation of physical properties.
show good tissue tolerance of the sites of implantations in the corneal stroma, without causing alteration of the epithelium and of the corneal endothelium
have, if possible, a low affinity for proteins,
be sterilizable and/or re-sterilizable.

GENERAL DESCRIPTION OF THE INVENTION

According to the present invention there is provided an uncrosslinked hydrogel with a relatively high water content, characterized in that it is constituted from a liquid starting composition (D) which comprises from 2 to 50% of a copolymer of acrylonitrile and an olefinically unsaturated comonomer bearing anionic groups, possibly salified, the molar ratio acrylonitrile-comonomer being comprised between 90:10 and 100:0, a suitable solvent and a suitable non-solvent of said copolymer, the ratio solvent/non-solvent being comprised between 500:1 and 0.5:1 by weight, said hydrogel having a microporous structure, an ionic capacity comprised between 0 and 500 mEq/kg of gel, a hydric content comprised between 50 and 98% and showing an aptitude for permanent deformation under stress, even at a temperature below 40° C.

According to an advantageous embodiment of said hydrogel, the molar ratio acrylonitrile-comonomer is preferably comprised between 95:5 and 99:1.

According to another advantageous embodiment of said hydrogel, the solvent is selected from the group which comprises aprotic polar organic solvents and/or inorganic solvents.

The solvents preferred are known solvents of said copolymers, preferably water-miscible; more specifically may be mentioned especially N,N-dimethyl formamide (DMF), dimethylsulfoxide (DMSO), N-methylpyrrolidone (2NMP), concentrated solutions of zinc chloride or of calcium chloride.

Such solvents enable particularly the production of hydrogels whose structure is particularly suitable for ophthalmological use and especially for keratophakia and epikeratophakia.

The hydrogels according to the invention have a residual content of solvent generally less than 1% and preferably less than 0.1%.

According to yet another advantageous embodiment of said hydrogel, the non-solvent is selected from the group which comprises water, aqueous solutions of a suitable inorganic salt and aqueous solutions of a suitable organic salt.

According to an advantageous disposition of this embodiment, when the non-solvent is an aqueous solution of salt, said solution is at a concentration comprised between 0.5 and 5%, so as to obtain in said composition (D), a salt concentration comprised between 0.33 and 1%, preferably between 0.05 and 1%.

The preferred mineral and organic salts are sodium or potassium chloride, sodium or potassium iodate, sodium or potassium bicarbonate, sodium or potassium chlorate, sodium or potassium periodate, sodium or potassium nitrate, sodium or potassium citrate, sodium or potassium tartrate, sodium or potassium ascorbate, sodium or potassium acette, sodium or potassium lactate.

According to a modality of this disposition, the preferred aqueous salt solution is a sodium chloride solution.

According to another preferred embodiment of the invention, the anionic groups are particularly selected from among the sulfonate, carboxyl, phosphate, phosphonate and sulfate groups.

The comonomer is advantageously sodium methallylsulfonate.

Such hydrogels, having a low electronegative charge, do not show interaction with the cells and hence have a distinctly improved tolerance.

It is also an object of the present invention to provide a process for the preparation of the uncrosslinked hydrogel according to the invention, characterized by the following steps:

(a) Lowering of the temperature of a liquid starting composition (D) comprising from 2 to 50% of a copolymer of acrylonitrile and an olefinically unsaturated comonomer bearing anionic groups, possibly salified, the molar ratio acrylonitrile-comonomer being comprised between 90:10 and 100:0, a suitable solvent and a suitable non-solvent of said copolymer, the ratio solvent/non-solvent being comprised between 500:1 and 0.5:1 by weight;

(b) immersion of the product in the course of gelification in a first suitable bath;

(c) then immersion of the hydrogel obtained in at least one suitable second bath, for a sufficient time to enable the stabilization of the hydrogel.

According to an advantageous method of practising the process according to the invention, the molar ratio acrylonitrile-comonomer is preferably comprised between 95:5 and 99:1.

According to another advantageous embodiment of the process according to the invention, the solvent is selected from the group which comprises aprotic polar organic solvents and/or inorganic solvents such as defined above.

According to another advantageous embodiment of said process, the non-solvent is selected from the group which comprises water, aqueous solutions of inorganic salt and aqueous solutions of organic salt.

According to an advantageous disposition of this embodiment, when the non-solvent is an aqueous salt solution, it is at a concentration comprised between 0.5 and 1%, so as to have in said composition (D) a salt concentration comprised between 0.03 and 1%, preferably between 0.05 and 1%.

The introduction of a non-solvent and particularly of the suitable aqueous salt solution, into the starting liquid composition can enable the production directly of a hydrogel whose structure and properties are entirely adapted to article for surgical or medical use.

According to yet another embodiment of said process, the bath of step (b) comprises advantageously at least water and/or an aqueous salt solution identical with or different from the non-solvent, when the latter is itself an aqueous salt solution.

According to an advantageous disposition of this embodiment, the immersion of step (b) is performed in two steps, the first step being an immersion in a cold water bath for a suitable time, the second step being an immersion in a water bath at room temperature for a suitable time.

This immersion in a cold water bath, in the course of the gelification, has the advantage of preventing the crumpling of the surface of the hydrogel during its formation, which would render the latter particularly useless in ophthalmology; in addition, the immersion of the gel in a water bath at room temperature, enables the complete removal of the solvent.

According to yet another embodiment of the process according to the invention, prior to step (c), the hydrogel is put into the form of a suitable article.

According to another method of practicing the process according to the invention, the bath of step (c) is selected from the group which comprises water and an aqueous salt solution at a temperature comprised between 0.5 and 5%, identical or different from the non-solvent when the latter is itself an aqueous salt solution.

According to an advantageous disposition of this embodiment, the immersion of step (c) is performed at a temperature comprised between room temperature and 70° C.

According to yet another advantageous embodiment, prior to the gelification step, the composition (D) is prepared by dissolving said copolymer in the solvent and the non-solvent, at a solution temperature comprised between 40° C. and 70° C.

According another advantageous embodiment of the invention, the temperature of cooling depends on the solvent and is advantageously comprised between −20° C. and +20° C.

Step (c) of the process of preparation of the hydrogel, namely the stabilization by immersion in a suitable solution (salt or water), enables a dimensional stabilization of said hydrogel (accelerated contraction or shrinkage process).

It is also an object of the present invention to provide an article for medical and/or surgical use such as tube, film, filament, joint, implant and the like, characterized in that it is constituted by and/or comprises a hydrogel according to the invention. According to an advantageous embodiment of the invention said article is in the form of an ocular implant.

Ocular implants according to the invention find application as intraocular, epicorneal, corneal implants as well as in orbito-palpebral and lacrymal plasties.

According to the invention, said shaped article may, then, be sterilized by any suitable means such as ultraviolet rays, ethylene oxide or ionizing radiations.

It is also an object of the present invention to provide a process for the manufacture of articles according to the invention, characterized in that an article of the desired shape and size is shaped from the hydrogel according to the invention.

According to a method of practising this process, said article is shaped prior to step (c) of the process of preparing the hydrogel according to the invention. According to an advantageous arrangement of this method of practice, the hydrogel is simultaneously prepared and shaped in a suitable mold.

According to another advantageous embodiment of this process, said article is shaped subsequent to step (c) of the process of preparation of the hydrogel according to the invention.

According to an advantageous arrangement of this embodiment, the hydrogel is heated to a temperature comprised between 50° and 90° C. and cast in a suitable mold in two parts.

According to another arrangement of this embodiment, said article is shaped by machining.

By machining, is meant, both mechanical machining and physical machining (U.V. laser).

According to the invention, when the article is shaped by molding, the mold is advantageously composed of two parts defining the concave and convex surfaces of the article, characterized in that said parts are of plastics material compatible with the solvent.

There may be mentioned particularly among plastics materials used poly-oxymethylene, polyolefines, polyamides, silicones and polytetrafluoroethylene (PTFE).

Besides the preceding arrangements, the invention comprises yet other arrangements, which will emerge from the description which follows, which refers to examples of practising the process and of producing implants, as well as a description of experiments both in vitro and in vivo.

It must be well understood, however, that these examples of practice, of production and of reports, are given purely by way of illustration of the invention, of which they do not constitute in any way a limitation thereof.

DESCRIPTION OF PREFERRED EMBODIMENTS

Example 1

Preparation of a hydrogel according to the invention containing 78% of water

1. Starting liquid composition (D):

9.6% of a 90:10 copolymer, of acrylonitrile and sodium methallylsulfonate (dry extract), 86.6% of dimethylformamide (DMF), 3.8% of 0.9% NaCl, in water.

2. Preparation of the starting solution:

The copolymer is dissolved in the form of a dry extract in DMF at a temperature of 70° C., by means of a ministirrer, for some minutes (5 minutes for 2 grams of solution, for example) then the 0.9% NaCl is introduced. It is homogenized by means of an ultrasonic sonotrode, for some seconds.

3. Casting:

Said starting solution, formed as specified at 2 is cast on a suitable support particularly a plate, at a temperature of 50° C.

4. Gelling:

The whole is cooled to a temperature of about −15° C. and

It is immediately dipped in a bath composed of 30% $C_2H_5OH$, 0.5% NaCl, 69.5% $H_2O$, at a temperature comprised between −10° and −5° C. for 5 minutes.

After dimensional stabilization, a hydrogel is obtained which contains 78% of $H_2O$.

Example 2

Preparation of a hydrogel according to the invention containing 80% of water

1. Starting composition:

9% of a 90:10 copolymer of acrylonitrile and of sodium methallylsulfonate (dry extract), 81% of dimethylformamide (DMF), 10% of 0.9% NaCl, in water.

2. Preparation of the starting solution:

The procedure is the same as that of Example 1, with the exception of the dissolving temperature which in this case is 40° C.

3. The procedure of step 3 is identical with that of Example 1.

4. Gelling:

(a) The whole is cooled to a temperature below or equal to 4° C. for 20 minutes.

(b) Immersion:

First step: the whole is dipped in water at about 0° C.–4° C. for 5 minutes.

Second step: then the whole is dipped for some minutes in water at room temperature, then the membrane obtained is separated and immersed from same hours in the same water.

5. Stabilization: The membrane is dipped for three hours in a 0.9% NaCl solution.

Example 3

Hydrogel according to the invention containing 90% of water

1. Starting composition:

5% of copolymer of arcylonitrile and sodium methallylsulfonate (dry extract), 80% of dimethylformamide (DMF) 15% of 0.9% NACl, in water.

2. Preparation of starting solution:

Procedure is the same as that of Example 1.

Steps 3, 4, and 5: the procedure is identical with that of Example 1.

Example 4

Hydrogel containing 86.6% of water:

Starting composition: 9% homopolymer (polyacrylonitrile) 81.1% of DMF 9.9% of 0.9% NaCl in water.

The other steps are identical with those of example 1.

Example 5

Ocular implant

The starting composition of Example 1 is cast directly on a suitable mold having the following characteristics:

The mold used in the present embodiment is a combination of polyamide - silicone. The mold is composed of a 6.6 polyamide support containing the concave part of unfilled silicone elastomer. The second part of the mold, convex, is a bead produced in elastomer-silicone of Shore A hardness 80, surface treated with an unfilled silicone, to improve the surface properties of said bead.

The concavity of the first portion of the mold was produced by the "spin-casting" method, by means of a rotating tray, specially designed and formed. The speed of rotation of the tray, variable and displayed, enables a desired height of a liquid meniscus to be obtained within a cylinder positioned on this plate.

Step 4 is identical with that of Example 1.

5. Stabilization: The formed article is dipped for 3 hours in a 0.9% NaCl solution.

6. Serialization: Seven minutes by means of ultra-violet rays. The implants must be checked both from the point of view of their optical qualities and their size and their tolerance both in in vitro and in vivo.

Example A

Macroscopic control of the intra-ocular implant

After having been dipped in physiological serum, the implant is checked under a binocular lens (dimensions, relief, optical homogeneity) on a black background, in incident light. The thickness of the implant was measured by a microfeeler. The radii of curvature were measured by means of a microslide reader, modified, so as to enable placing under the objective lens of a cup containing the immersion liquid and the lens. The projection of the profile of the lens, focused on the median section, was traced and the rays measured with a compass.

The implants formed and tested had the following characteristics:
diameter: 6 mm.
central thickness of the order of 0.2 mm.

Example B

Physicochemical properties of the implant (a) Linear shrinkage:

The measurements were performed on specimens having as initial sizes: 75×25×0.8 mm.

The shrinkage of the hydrogel according to the invention, is distinctly greater in the presence of a saline solution (0.9% NaCl), as shown by Table 1 below:

TABLE I

| INITIAL COMPOSITION | SHRINKAGE L/L · 100 (%) | | | |
|---|---|---|---|---|
| of the mixture: P/S/NS | IN H$_2$O | % H$_2$O | In Serum | % H$_2$O |
| 5,3/83,5/11,2 | 3.9 | 94 | 27.6 | 86 |
| 7,0/82,5/10,5 | 5.2 | 91 | 27.6 | 82 |
| 9,0/81,0/10,0 | 6.6 | 88 | 24.3 | 81 |
| 11,0/80,0/9,0 | 7.9 | 86 | 21.7 | 80 |
| 13,0/79,0/8,0 | 9.2 | 85 | 18.4 | 79 |
| 19,0/75,0/6,0 rapid gelling | 15.7 | 78 | 17.0 | 72 |
| 5,1/80,0/14,8 | 4.8 | 95 | 19.7 | 90 |

P: Polymer; S: Solvent; and NS: non-solvent.

This phenomenon has its limits and the shrinkage is only manifested up to a certain concentration of solute. For example, the gel dipped in 0.9% NaCl solution (physiological serum) shows a shrinkage of 21.7%. The same gel dipped in a 5% NaCl solution has almost the same shrinkage of about 23%.

(b) water permeability, to physiological serum, to small and medium molecules:

This is one of the fundamental properties of materials for use in corneal refractive surgery and particularly for intracorneal implants. This permeability is an essential result for the maintenance of the corneal physiology on which the transparency of the cornea depends. Nutrient and metabolic flows, the transport of dissolved gases (oxygen and carbon dioxide), water migration, must not be hindered by the presence of the lens.

The implants according to the present invention show through their particular structure very good permeability. The permeability to water, to physiological serum and to various dissolved substances, was measured by means of a test bench constituted by a tank provided with a stirrer. The membrane tested was placed in sealed manner in contact with a 6.6 polyamide support. Hence it separates the tank into compartments: that of the solution—that of the filtrate.

All the measurements were carried out on samples of hydrogel of copolymer, according to the invention, containing 80% of H$_2$O, in the form of membranes of a thickness of 0.35–0.40 mm and of 18 cm$^2$ surface. They were packaged in physiological serum. The pressure gradient was maintained at 20 cm at H$_2$O.

The permeability to small and medium molecules was evaluated by the transmittance coefficient K expressing the ratio of the concentrations of the substance in the filtrate and in the solution for a stable flow rate and at room temperature.

| | | $K = \dfrac{C\ \text{filtrate}}{C\ \text{solution}}$ | |
|---|---|---|---|
| Subs. | Conc. g/l | FLOW RATE $10^{-5}$ ml/ mn · cm$^2$ · mmHg | TRANSMITTANCE COEFFICIENT |
| water | | 4.5 | — |
| NaCl (serum) | 0.09 | 3.5 | — |
| urea | 0.7 | 4.0 | 1 |
| creatinine | 0.05 | 2.7 | 0.98 |
| glucose | 1.1 | 2.7 | 1 |
| vitamin B$_{12}$ | $2.10^{-2}$ | 3.2 | 1 |
| albumine H | 40.0 | 1.9–1.6 | 0.4 |

(c) permeability to oxygen:

Tests were carried out on specimens of membrane of hydrogel:

containing 80% of water (hydrogel according to the invention), and 70% of water, having a thickness of 0.15–0.25 and 0.37 mm.

The permeability to oxygen was: $35-36.10^{-11}$ ml/cm$^2$/cm.s.mm Hg, for 80% water hydrogel, whilst it is only $29.10^{-11}$/cm$^2$/cm.s.mm Hg, for a 70% ware hydrogel.

(d) Refractive index:

It was measured by means of an ABBE refractometer (CARL ZEISS COMPANY, W-GERMANY). The results are shown in Table 2 below and relate to membranes of hydrogel.

TABLE II

| SPECIMEN | REFRACTIVE INDEX |
|---|---|
| Hydrogel 85% H$_2$O | 1.347 |
| Hydrogel 83% H$_2$O | 1.350 |
| Hydrogel 78% H$_2$O | 1.368 |

Figure 1:
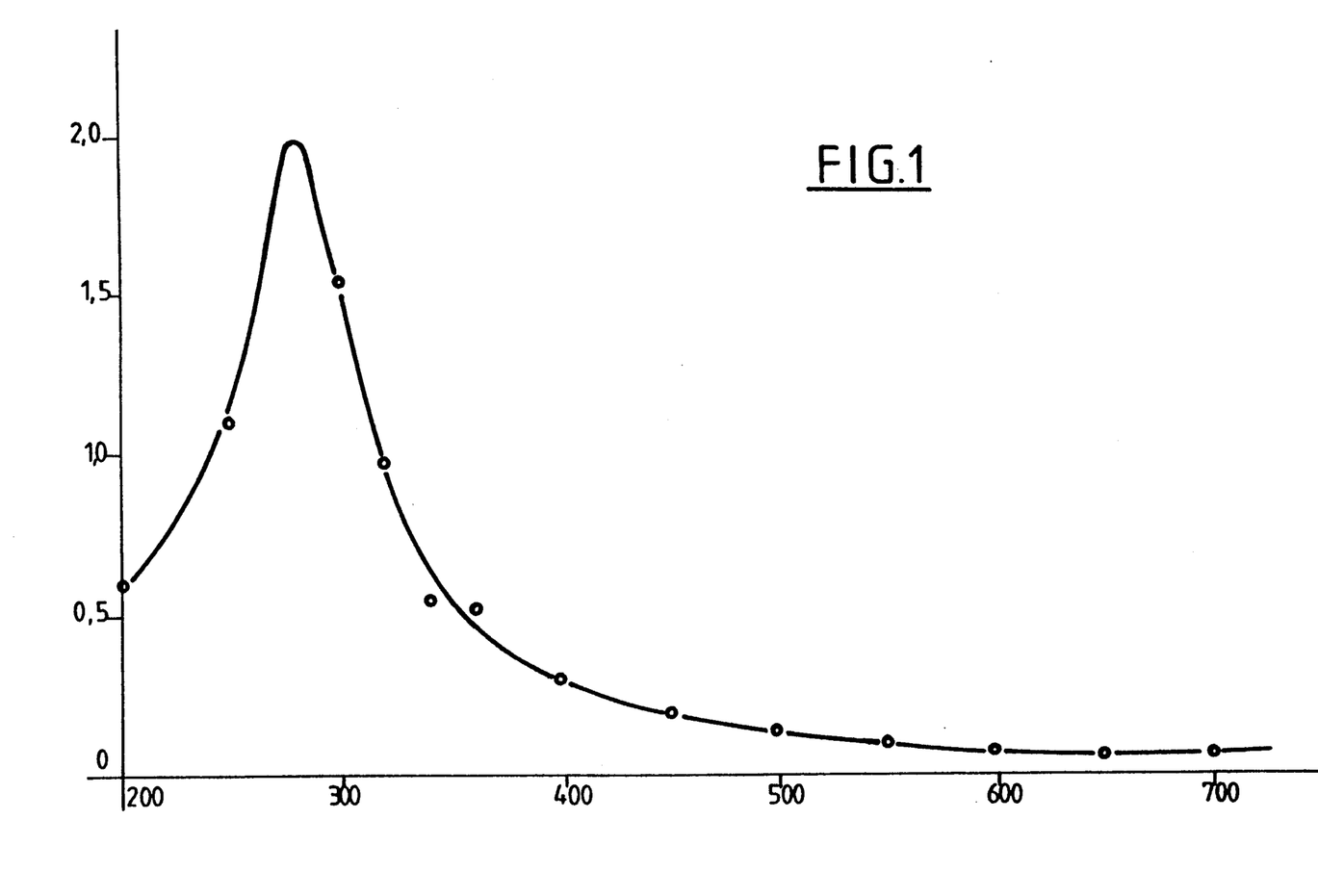
FIG. 1 shows the absorption of light by the implant. The ordinate axis is the absorbance and the abscissae axis is the wavelength.

(e) absorption of light (visible light and ultra-violet light):

This measurement was carried out on specimens of the hydrogel according to the invention, containing 80% of water, by a spectrophotometric method. FIG. 1 shows the absorption of light by the implant.

The ordinate axis represents the absorbance:

$$A = -\log (I_f/I_i).$$

If being the intensity of the light which has passed through and Ii, the intensity of the initial light. The abscissae axis represents the the wavelength in mm.

It is seen that there is total absorption at 280 nm whilst there is no absorption for visible light (400-70 nm).

Figure 2:
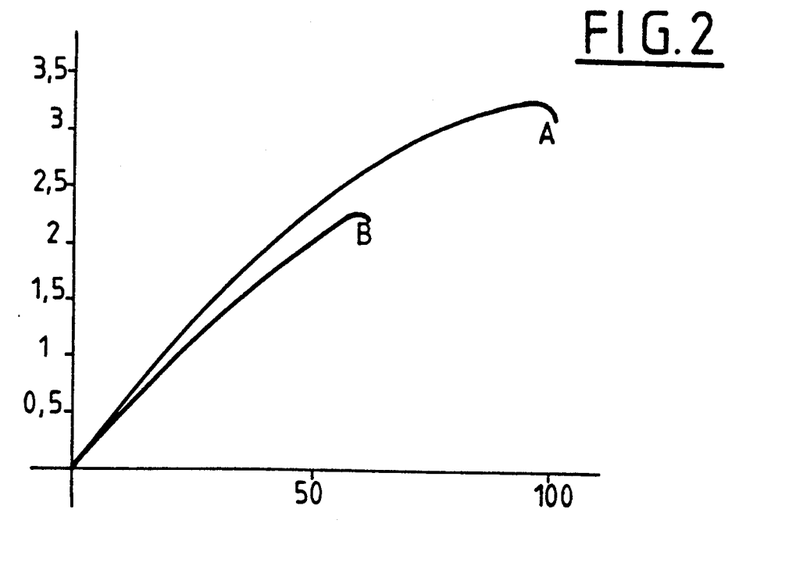
FIG. 2 shows tensile strength versus water content of hydrogel. The abscissae axis represents the percent elongation and the ordinate axis the load in Kg/Cm.$^2$

(f) Mechanical tests:

FIG. 2 shows that in spite of a high water content, the tensile strength is fairly high.

The abscissae axis represents the % elongation and the ordinates axis the load in kg/cm². Curve A corresponds to a hydrogel with 80% water. Curve B corresponds to a hydrogel with 85% water.

Example C

"In vitro" evaluation of a hydrogel utilizable as an intra-corneal implant

Tissue used:

Chicken embryo corneal endothelium of 14 days incubation.

Materials:

Positive control (toxic): a filtering disk (Millipore AP25 1300) soaked in a phenol solution with 64 mg/l in culture medium (ph 1/100);

Negative control (non toxic): Thermanose (Lux Corpo.) plastic treated for cell cultures (THX).

A hydrogel according to the invention (80% to 90% H₂O) sterilized with UV and tyndalised at the time of use (H1).

A membrane of 22 μm thick polyacrylonitrile for hemofiltration (Hospal) (H2).

Culture Technique

The culture medium was DMEM mixed V/V with gelose and supplemented with 10% of foetal calf serum. Whole corneal fragments were cultivated on the endothelial surface in contact with different materials and controls.

Evaluation Criteria

All the measurements were carried out on the same batch of 24 explants for each type of tissue and each material, after 7 days of culture. The following three properties were measured quantitatively: multiplication, migration and cellular adhesion by measurement of the surface area of migration of the cells and counting of cells of this migration web.

Cellular Multiplication and Migration

The results are expressed by the cell density as a function of the migration surface area.

Cell Adhesion

The technique of sensitivity of the cells to trypsin was used, which permitted calculation of the percentage of the cells detached as a function of time and the establishment of the corresponding curve.

From this curve, a static adhesion index (SAI) was defined which is the product of the area (A) comprised between the curve and the x axis and the total number of cells. The results are expressed by the area of the curve as a function of the SAI.

Results and Interpretation

The results are summarized in Table III below:

The toxic control (ph 1/100) occurs in the limiting area of the diagram of multiplication and of migration.

It shows a slight toxicity with respect to corneal endothelium and permits very average cell attachment. The non-toxic control permits very slight multiplication of the endothelial cells of the cornea which adhere to a very moderate degree to it surface.

H2 facilitates a high migration of the endothelium and consequently low adhesion.

Figure 3:
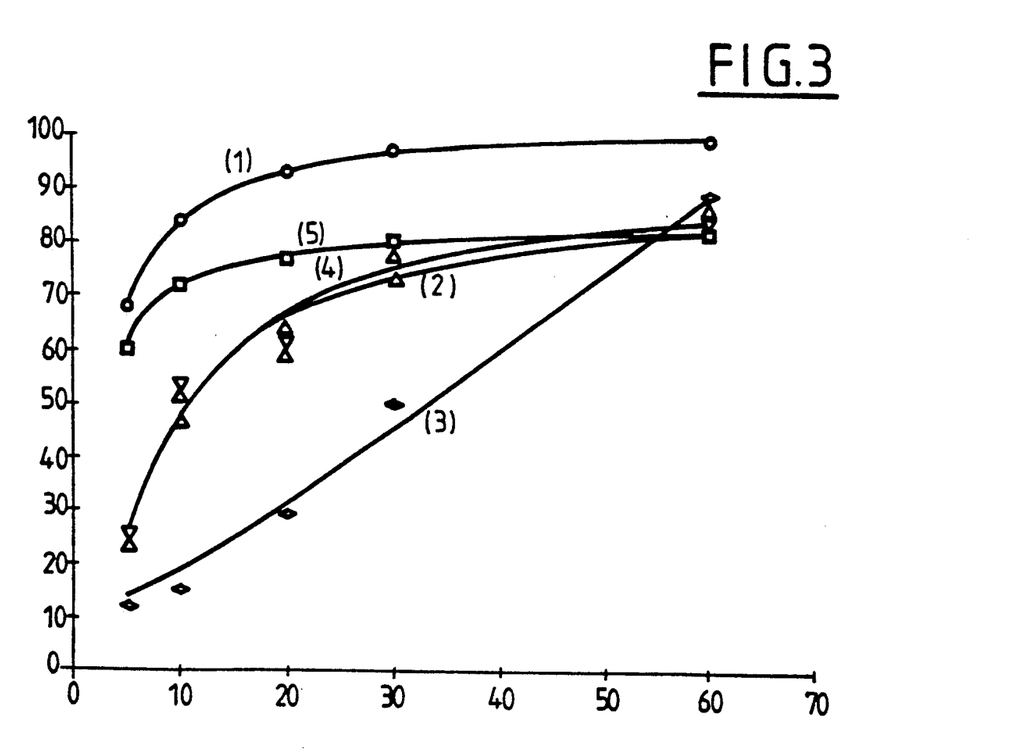
FIG. 3 represents the percent of cells detached as a function of time. The abscissae axis represents time and the ordinate axis the percent of cells detached.

H1 enables multiplication of the endothelial cells superior to that of the negative control and shows a distinctly superior cell attachment to that of all the other materials which is very well demonstrated by FIG. 3 (% of cells detached as a function of time), in which the abscissae axis represents time in min and the ordinates axis represents the percentage of cells detached. In this figure, the curve (1) corresponds to H2, the curve (2) to the toxic control, curve (3) to the product according to the invention, curve (4) to the non-toxic control and curve (5) to PVC. Example D: In vivo corneal tolerance test:

Implants of copolymers according to the invention, were implanted unilaterally in the cornea of six cats and nine monkeys.

These implantations permitted the evaluation of biocompatibility of the implants and their transparency.

The operational technique calls upon either an intra-stromal lamellar dissection, or, so far as possible, a lamellar dissection with the BARRAQUER microkeratome.

The BARRAQUER micro-keratome, to be realisable, necessitates the fixing of the eyeball by a pneumatic ring. This dissection has the advantage of sectioning in totality the Bowman membrane and of permitting the deformation of the front layers of the cornea of the implant.

1. Implantation in the cat

Lamellar dissections were carried out with the manual disciser.

Operational Procedure

General anesthesia is performed by sub-cutaneous injection of ketamine (about 30 mg/kg weight) and oxybuprocaine is instilled systematically into the eye.

A slightly arc-shaped incision with internal concavity is made at 0.25 mm depth and to 2 mm into the limb, over about 8 mm length. This incision necessitates the use of a micrometric knife with a diamond blade. The lamellar dissection is continued with a Beaver disecter and with a Paufique disector over about 9 to 10 mm.

The intraocular implants were placed in position by means of a metal spatula. The sutures were done with 10/0 monofilament of polyamide and left in place for 10 days.

After placing the implants in position, a collyrium containing dexamethasone and neomycine was instilled daily into the operated eye for a month. The cats were

TABLE III

| | NUMBER OF CELLS | l | dC | A | SAI × 10⁶ |
|---|---|---|---|---|---|
| THX | 8150 ± 3000 | 4.9 ± 1.8 | 1800 ± 1000 | 4600 ± 600 | 0.36 ± 0.1 |
| PH 1/100 | 8100 ± 3500 | 2.6 ± 0.8 | 3000 ± 350 | 4900 ± 100 | 0.4 ± 0.1 |
| H1 | 16603 ± 245 | 6.6 ± 0.4 | 2500 ± 118 | 2500 ± 315 | 0.42 ± 0.06 |
| H2 | 39700 ± 7000 | 23 ± 9 | 1730 ± 100 | 5170 ± 300 | 205 ± 0.9 | examined daily through the duration of the experiment. Technical characteristics of the implants:

the water content of the implants was 80% of water;
the implants had a diameter of 5.5 to 6.3 mm, their thickness ranging from 0.20 to 0.2 mm.

The results observed in the cat were good tolerance of the keratoprothesis, without necrosis of the receptor cornea.

2. Implantation in the primate

Operational procedure

Nine female papio cynocephalus monkeys (baboons) were operated on.

In three cases, a lamellar dissection was performed by a technique identical with that used in the cat; they were in fact small sized monkeys, not permitting the fixation of the eyeball by a pneumatic ring. In the six other cases, lamellar dissection with the microkeratome was possible.

Technical Characteristics of the Implants the water content of the implants was 60, 70, and 80% water;
the diameter of the implants range from 4.8 to 7 mm;
thickness of the implants ranged from 0.16 to 0.27 mm.

Results

The transparency of the cornea and the transparency of the implant were remarkable.

As emerges from the foregoing the invention is in no way limited to those of its embodiments, methods of practice and use which have just been described more explicitly: it encompasses thereof on the contrary all modifications which may come to the spirit of the technician skilled in the art, without departing from the range or the scope of the present invention.

We claim:

1. An ocular implant having good tissue tolerance at the site of implantation comprising an uncrosslinked hydrogel with a high water content, obtained from the following liquid starting composition:

2 to 50% by weight of a copolymer of acrylonitrile and an olefinically unsaturated comonomer bearing anionic groups, said comonomer selected from the group consisting of methallylsulfonic acid, methallylcarboxylic acid, methallylphosphoric acid, methalylphosphonic acid and methallylsulfiric acid, in an acrylonitrile/comonomer molar ratio of at least 90:10;

a suitable solvent of said polymer selected from the group consisting of aprotic polar organic solvents and inorganic solvents; and a suitable non-solvent of said polymer selected from the group consisting of aqueous solutions of a suitable inorganic salt and aqueous solutions of a suitable organic salt, wherein the ratio of the solvent to the non-solvent is between 500:1 and 0.5:1 by weight of the composition; and wherein said hydrogel has a microporous structure, an ionic capacity between 0 and 500 mEq/Kg of hydrogel, a hydric content between 50 and 98% by weight, an aptitude for permanent deformation under stress at temperatures below 40° C., and wherein said ocular implant has the following physicochemical characteristics:

permeability to physiological serum and to small and medium molecules, permeability to oxygen of $36.10^{-11}$ mg/cm$^2$/cm.s.mmHG for a hydrogel with a hydric content of 80%, no absorption of visible light (400–700 nm), a tensile strength of 2 kg/cm2 for 50% elongation, and a refractive index lower than 1.368.

2. The ocular implant of claim 1, wherein said acrylonitrile and said comonomer are present in said hydrogel in a molar ratio between 95:5 and 99:1, inclusive.

3. The ocular implant of claim 1, wherein said comonomer is salified.

4. The ocular implant of claim 3, wherein said comonomer is sodium methallylsulfonate.

5. The ocular implant of claim 1, wherein the non-solvent of said polymer is an aqueous solution of a suitable salt, having a concentration between 0.5% and 5% by weight, such that when added to the liquid starting composition, the salt concentration therein is between 0.03% and 1% by weight of the composition.

6. The ocular implant of claim 1, wherein the non-solvent is an aqueous solution of sodium chloride.

7. The ocular implant of claim 1, wherein the solvent is selected in the group consisting of N,N-dimethyl formamide (DMF), dimethylsulfoxide (DMSO), N-methylpyrrolidone (2NMP).

8. The ocular implant of claim 1, obtained from said liquid starting composition wherein the composition is cooled and simultaneously immersed into a bath of a mixture of an organic non-solvent and a mineral non-solvent in water and stabilized.

9. The ocular implant of claim 1, wherein the immerging bath comprises $C_2H_5OH$, NaCl 0.9% and water.

* * * * *

UNITED STATES PATENT AND TRADEMARK OFFICE
CERTIFICATE OF CORRECTION

PATENT NO. : 5,273,750

DATED : December 28, 1993

INVENTOR(S) : Jiri Honiger et al.

It is certified that error appears in the above-identified patent and that said Letters Patent is hereby corrected as shown below:

On title page, item [19] and [75] the
first inventor's last name which appears as "Homiger" should be -- Honiger --.

On title page, item [54] in the title
the word -- Filaments -- should be inserted after the word "Tubes," and before the word "Films,".

Item [57] ABSTRACT
line 9, "aninic" should be -- anionic --.

Column 1, in the title, the word -- Filaments -- should be inserted after the word "Tubes," and before the word "Films,".

Column 1, line 49, "described" should be -- describes --.

Column 3, line 7, "0.33" should be -- 0.03 --.

Column 3, line 15, "acette" should be -- acetate --.

Column 3, line 63, "1%" should be -- 5% --.

Column 6, line 31, "from same" should be -- for some --.

Column 7, line 44, Table I in the heading, "P/S/NS" should be -- P/S/NS% --.

UNITED STATES PATENT AND TRADEMARK OFFICE
CERTIFICATE OF CORRECTION

PATENT NO. : 5,273,750

DATED : December 28, 1993

INVENTOR(S) : Jiri Honiger et al.

It is certified that error appears in the above-identified patent and that said Letters Patent is hereby corrected as shown below:

Column 9, line 6, "70" should be -- 700 --.

Column 11, line 52, "methallylsulfiric" should be -- methallylsulfuric --.

Column 12, line 21, "mg/cm$^2$/cm.s.mmHG" should be -- ml/cm$^2$/cm.s.mmHg--

Signed and Sealed this

Fourteenth Day of June, 1994

Attest:

BRUCE LEHMAN

*Attesting Officer*     *Commissioner of Patents and Trademarks*